United States Patent [19]
Puski et al.

[11] Patent Number: 4,830,861
[45] Date of Patent: May 16, 1989

[54] LOW MANGANESE HIGH PROTEIN RICE FLOUR

[75] Inventors: Gabor Puski, Newburgh; John R. Euber; Grant H. Hartman, Jr., both of Evansville, all of Ind.

[73] Assignee: Bristol-Myers Company, New York, N.Y.

[21] Appl. No.: 219,535

[22] Filed: Jul. 14, 1988

[51] Int. Cl.$^4$ .......................... A23L 1/29; A21D 2/22; A23C 9/20
[52] U.S. Cl. ........................................ 426/18; 426/28; 426/52; 426/622; 426/629; 426/801
[58] Field of Search ...................... 426/18, 28, 52, 622, 426/629, 801

[56] References Cited

U.S. PATENT DOCUMENTS

| | | | |
|---|---|---|---|
| 3,932,671 | 1/1976 | Yokotsuka et al. | 426/18 |
| 3,958,015 | 5/1976 | Gay | 426/18 |
| 4,282,319 | 8/1981 | Conrad | 426/18 |
| 4,431,674 | 2/1984 | Fulger et al. | 426/18 |
| 4,448,790 | 5/1984 | Sarkki et al. | 426/18 |
| 4,744,992 | 5/1988 | Mitchell et al. | 426/52 |

OTHER PUBLICATIONS

Hansen et al., *Food Technology*, 35 (No. 11), 38–42 (1981).
Chen etal., *J. Sci. Food Agric.* 35, 1128–1135 (1984).
Chang et al., *Journal of Food Science*, 51 (No. 2), 464–467 (1986).

*Primary Examiner*—Donald E. Czaja
*Assistant Examiner*—Helen Pratt
*Attorney, Agent, or Firm*—Robert H. Uloth

[57] ABSTRACT

A method for preparing high protein rice flour (HPRF) containing low manganese is disclosed wherein essential steps comprise:

blending rice flour and water at a pH of 3.4 to 4.6;
separating the insoluble washed rice flour;
resuspending the washed rice flour and adjusting the suspension to a pH and temperature within the operable range of an alpha-amylase enzyme;
treating the suspension with an alpha-amylase enzyme for a sufficient time to hydrolyze the starch to 5 to 50 DE content;
adjusting the treated mixture to a pH of 3.4 to 4.6; and the
separating rice syrup from low manganese high protein rice flour.

The high protein rice flour contains more than 16% protein, has a manganese content of 50 micrograms or less per gram of protein and is further treated with a proteolytic enzyme to provide a modified low manganese HPRF suitable for use in powdered infant formula.

26 Claims, No Drawings

LOW MANGANESE HIGH PROTEIN RICE FLOUR

BACKGROUND OF THE INVENTION

1. Field of the Invention

The present invention relates to rice-based food compositions and to their methods of preparation. More particularly, the present invention relates to high protein rice flour (HPRF) nutritionally complete formulas and most particularly to infant formula. In its methods aspect, the present invention relates to methods for preparing high protein rice flour suitable for use in rice-based infant and adult nutritional formulas.

2. Description of the Prior Art

Rice is a starchy food containing approximately 6-10% protein. Rice flour, as a raw material of nutritional value, constitutes an inexpensive by-product of rice milling obtained by grinding broken rice. Conventional milling practices produce rice flour composed largely of about 80% carbohydrate with about 7-9% protein material. However, the PER (protein efficiency ratio-ratio of weight gain of rats to protein consumed of a 10% protein diet) for rice is 2.18 which is almost equivalent to that of beef (2.30), a considerably more costly protein source. Because of the low concentration of protein in rice and the resulting bulk required to obtain a satisfactory protein intake, infants and children cannot eat a sufficient amount to meet their protein requirements.

Efforts to improve the protein quantity of rice involving selected breeding of new rice varieties have not met the protein content required by young children. Research directed to the production of rice flour with increased protein content has been conducted. Prior art within this general area includes the following papers.

Hansen, et al., *Food Technology*, 35 (No. 11), pages 38-42 (1981) developed a high protein rice flour (25% protein content) by using the enzyme alpha-amylase to digest the starch material of milled broken rice thereby decreasing starch content resulting in increased protein content compared to the original rice flour. In the Hansen, et al. process, a 5% slurry of finely ground crude rice flour is first heated for 30 min. at 100° C. to effect gelatinization, then partially digested by enzyme (alpha-amylase) treatment, centrifuged and the precipitated HPRF freeze-dried. Protein level of HPRF was reportedly increased three-fold over the starting material (approximately from about 8% to 25%). The supernatant is principally carbohydrate (98.3%).

Chen, et al., *J. Sci. Food Agric.* 35, 1128-1135 (1984) modified the Hansen et al. process to provide both HPRF and high-fructose rice syrup from broken rice. In the Chen, et al. process, a 20% slurry of the milled broken rice is mixed with calcium chloride (70 mg/kg rice), pH adjusted to 6.5 and digested (liquified) with alpha-amylase optimally at 90° C. for 90 min.; specifically with Termamyl 60L alpha-amylase obtained from NOVO Industri, A/S, Denmark. The liquified mixture is centrifuged and the precipitated HPRF dried. Protein content of the HPRF was similar to Hansen, et al. (approximately three times as high as the raw material). The supernatant is saccharified at 60° C. with glucoamylase and then isomerized to fructose with glucose isomerase to provide a high-fructose rice syrup containing 50% glucose, 42% fructose and 3% maltose.

Chang, et al., *Journal of Food Science*, 51 (No. 2), pages 464-467 (1986) further modified the Hansen, et al. process to produce a rice flour with increased protein and calcium contents. According to Chang, et al., processing conditions for the production of HPRF concerned treating gelatinized rice flour slurry with calcium chloride and alpha-amylase 60° C. for 90 min. The hydrolyzed starch is removed by centrifugation and the precipitated paste freeze dried to yield high protein rice flour with approximately 38% protein, a PER ratio of 2.17 and an amino acid composition similar to the rice flour of Hansen, et al.

It is evident that the prior art mentioned above describes a fundamental process for preparation of high protein rice flour (HPRF) wherein rice flour is gelatinized and enzymatically digested with carbohydrate-type enzymes commonly known as amylases. This treatment hydrolysis the starch to soluble saccharides of various molecular weights such as glucose, maltose, oligosaccharides, and dextrins from which the insoluble HPRF is separated, for example by centrifugation. Thus, by partial removal of the non-proteinaceous material, the processed rice flour contains less carbohydrate and the protein content is correspondingly enhanced.

High protein rice flour obtained as described in the prior art has not proved to be entirely satisfactory as a raw material for nutritional products. For instance, over 80% of rice protein consists of glutelin which is completely insoluble at pH's acceptable for infant formula. Infant formulas made with such protein do not form satisfactory dispersion, have a very grainy, gritty mouthfeel and tend to plug up the nipple. Moreover, the HPRF prior art process does not address the problem of unacceptable manganese levels. The manganese content of commercially available rice flour varies considerably with a typical content of about 150-260 micrograms (mcg) per gram protein. Table I below illustrates observed variations in manganese content of representative commercial rice flours containing about 8% protein.

TABLE I

| Manganese Content of Commercial Rice Flours | |
|---|---|
| Source | Manganese, mcg/g Protein |
| Riceland Foods[a] | 150-163 |
| California Rice Growers Association[b] | 150-200 |
| Riviana Rice Flour[c] | 150-250 |
| Coor's rice flour[d] | 220-260 |

[a]Stuttgart, AR
[b]Sacramento, CA
[c]Houston, Texas
[d]ADM Milling, Rice Div., Weiner, AR We have determined that using such rice flour as raw material in the conventional prior art process (gelatinization and enzymatic digestion) results in a concomitant enrichment of manganese along with increased protein content. Apparently, the manganese associates with the protein and remains with the separated HPRF rather than the solubilized saccharides.

Manganese is considered an essential element in the mammalian diet. It is also known that only relatively small quantities are required by human infants. Human milk levels are generally below 32 micrograms per quart and pediatric nutritionists favor infant formula with relatively low manganese levels. The National Academy of Sciences-Food and Nutrition Board (NAS-FNB) has determined the U.S. average daily intake and the estimated safe and adequate daily dietary intake as follows.

| Dietary Intake | |
|---|---|
| U.S. Avg. Daily Intake | |
| Infants | 10–300 mcg/day |
| Children, 3–5 yrs. | 1,400 mcg/day |
| Children, 10–13 yrs. | 2,180 mcg/day |
| Adults | 2,500–9000 mcg/day |
| Estimated Safe and Adequate Daily Dietary Intake | |
| Infants 0–6 months | 500–700 mcg/day |
| Infants 6–12 months | 700–1000 mcg/day |
| Children and Adolescents | 1,000–3,000 mcg/day |
| Adults | 2,500–5,000 mcg/day |

A quart of infant formula typically contains about 14–20 g protein. As previously mentioned, the HPRF of the prior art retains substantially all of the manganese found in rice flour raw material which has typical manganese levels of 150–260 micrograms per gram protein. Thus, the amount of manganese in a quart of rice protein based infant formula containing 14 to 20 grams protein is calculated as follows for particular levels of rice flour manganese content.

CALCULATION 1
Manganese Per Quart Formula From Rice Flour
(grams protein × mcg manganese per gram)

| Mn Content of Rice | Micrograms Manganese per Quart | |
|---|---|---|
| Flour (mcg/g) Protein | 14 g protein | 20 g protein |
| 150 | 2100 | 3000 |
| 260 | 3640 | 5200 |

With the assumption that an infant's diet includes one quart of formula per day, rice flour as a source of protein can contain a maximum of about 50 mcg of manganese/g protein (estimated maximum safe and adequate daily dietary manganese intake of 700 mcg/day divided by 14 grams of protein). Since rice flours generally available contain considerably more than 50 mcg manganese/gram protein, they cannot be used to make HPRF suitable for infant formula.

SUMMARY OF THE INVENTION

It is an object of the present invention to provide a high protein rice flour (HPRF) with low levels of manganese relative to protein which can be used in infant nutritional formulas. The HPRF of the invention is characterized in that it has a protein content of greater than 16%, preferably 16 to 60% and a manganese content of 50 micrograms or less per gram protein. Preferred and practical operable ranges for the instant HPRF is 5 to 50 mcg manganese/gram protein with a typical production scale process of from 10 mcg/g protein to 30 mcg/g protein.

A second object is to improve the mouthfeel of the instant HPRF.

Another object is to provide a new and improved process for producing HPRF wherein low levels of manganese relative to protein are obtained.

A further object of the invention is to provide a nutritionally complete rice based infant powder formula having less than 700 micrograms of manganese per quart when reconstituted.

These objects, as well as others apparent from the specification, are achieved by the instant invention in accordance with the detailed description below.

Briefly, according to the invention, there is provided a process (herein Process A) for preparing high protein rice flour (HPRF) with substantially reduced manganese content from rice flour containing manganese which comprises the steps of:
(Aa) blending rice flour and water at a pH of 3.4 to 4.6;
(Ab) separating the insoluble washed rice flour of step (Aa);
(Ac) resuspending the washed rice flour of step (Ab) and adjusting the suspension to a pH and temperature within the operable range of an alpha-amylase enzyme;
(Ad) treating the pH and temperature adjusted suspension of step (Ac) with an alpha-amylase enzyme for a sufficient time to hydrolyze the starch to 5 to 50 DE content;
(Ae) adjusting the treated mixture of step (Ad) to pH of 3.4 to 4.6; and then
(Af) separating rice syrup from low manganese high protein rice flour.

Further in accordance with the invention, a process is provided for converting the low manganese high protein rice flour (HPRF) by enzymatic hydrolysis to provide a low manganese HPRF hydrolysate with dispersibility and mouthfeel characteristics suitable for liquid or powdered infant formula. The process comprises the steps of:
(a) adjusting a slurry of said low manganese HPRF to conditions optimum for protease enzyme;
(b) adding a proteolytic enzyme;
(c) stirring the mixture for a sufficient period to hydrolyze from 1 to 5% of the peptide bonds; and then
(d) heating the mixture to 70° to 80° C. to inactivate the proteolytic enzyme.

The hydrolysate can be partially concentrated by conventional means such as evaporation and then spray dried to provide a low manganese HPRF hydrolysate powder base which can be used in infant formulas.

DETAILED DESCRIPTION OF THE INVENTION

The process of the invention for preparing high protein rice flour (HPRF) with reduced manganese content is applicable to rice and in particular to whole kernel polished rice, rice grits and rice flour. In general, rice flour from about 90 to 120 mesh obtained by grinding broken rice constitutes preferred raw material as it is a by-product of rice milling, readily available, and relatively inexpensive. Detailed discussion of process steps follow and for purposes of the instant specification and claims, the following terms are defined.

High protein rice flour—processed rice flour having at least 16% protein.

Rice syrup—water soluble rice carbohydrate.

Low manganese HPRF—high protein rice flour containing 50 mcg or less manganese per gram protein.

High manganese HPRF—high protein rice flour containing more than 50 mcg of manganese per gram protein.

Modified low manganese HPRF—proteolytic treated low manganese HPRF containing 50 mcg or less manganese per gram protein with improved dispersibility and mouthfeel compared to low manganese HPRF.

Blending rice flour and water at pH 3.4 to 4.6 and separating the insoluble washed rice flour—steps (Aa) and (Ab)

The initial step in Process A of the present invention involves washing rice flour containing more than 50 mcg manganese per gram protein. As previously mentioned, commercially available rice flour generally contains from 150-260 micrograms manganese per gram protein and the instant process is particularly suited to reducing manganese levels of the high protein rice flour obtained therefrom to levels of 50 microgram or less manganese per gram protein. This is conveniently carried out by continuous blending the rice flour and water with sufficient food-grade acid to maintain a pH in the range of 3.4 to 4.6. The method of washing (e.g., batchwise or continuous) is not particularly critical as long as conditions provide thorough mixing. Both organic acids such as acetic, citric, and inorganic acids such as sulfuric, hydrochloric, nitric and phosphoric may be used for pH adjustment.

Sufficient water is used to provide a pumpable slurry. For example, a flour-water ratio (parts by weight) of about 1:3-20 is operable for commercial production with a flour-water ratio of 1:6-12 preferred and 1:9 most preferred. More dilute solutions can be employed if desired. For instance, three percent suspensions (flour-water ratio of about 1:33) of rice flour containing about 140 mcg/g protein of manganese adjusted to pH 3.5 with hydrochloric, nitric, sulfuric, acetic or citric acid stirred at ambient temperature for one hour and centrifuged provided rice flour with Mn levels of 15 mcg/g protein or less. Use of relatively large amounts of acid wash on a commercial scale is impractical and uneconomical because of the problems involved in handling and disposing the spent wash. In the above illustration, each pound of HPRF requires about 33 pounds of acid wash and on a tonage basis represents a major environmental consideration.

With reference to the pH range of 3.4 to 4.6 for blending the rice flour and water, a pH lower than about 3.4 tends to solubilize a significant amount of protein and use of pH higher than about 4.6 lessens the amount of manganese removed from the rice flour. The preferred blending step range is a pH of 3.8 to 4.2 wherein yields and low manganese levels are optimized.

Temperature at which the blending (washing) step is conducted is not particularly critical and the washing step is conveniently carried out at ambient temperature generally from about 10° to 30° C., preferably at about 20°-25° C. Higher temperatures above 65°-70° C. known to cause gelatinization of rice starch should be avoided because of excess water retention resulting from increased viscosity which significantly diminishes the amount of manganese removed.

Blending and separation (e.g., by centrifugation or other conventional means) of the washed rice flour is generally completed in from 10 minutes to 90 minutes but the length of the washing period has no appreciable effect on the degree of manganese removed and longer periods can be employed if desired for operating convenience.

Table 1 below sets out results obtained by washing 8% protein rice flour (1:9 flour-water ratio) containing 260 mcg manganese/g of protein at pH 3.5 for various times and temperatures indicating these variables have a relatively small effect on manganese removal.

TABLE 1

Effect of Time and Temperature on Removal of Manganese from Rice Flour by Acid Washing

| Time (Min.) | Temperature (°C.) | mcg Mn/g Protein (washed flour) | Percent Mn Removed From Rice Flour |
|---|---|---|---|
| 0[a] | 13 | 63 | 76 |
| 15 | 13 | 70 | 73 |
| 30 | 13 | 59 | 77 |
| 60 | 13 | 59 | 77 |
| 120 | 13 | 65 | 75 |
| 15 | 19 | 68 | 74 |
| 15 | 49 | 60 | 77 |

[a]Immediately centrifuged following mixing.

The efficiency of manganese removal from rice flour by acid washing can be increased by the addition of relatively small amounts of calcium salts. Various calcium salts such as calcium chloride, monobasic calcium phosphate, dibasic calcium phosphate, tribasic calcium phosphate enhances manganese removal as shown in Table 2 below wherein results obtained by washing rice flour (1:9 flour-water ratio) containing 260 mcg/g protein manganese at pH 3.5 with calcium chloride are set forth.

TABLE 2

Effect of Calcium Chloride on Manganese Removal During Acid Washing

| Calcium chloride added (% of rice flour) | mcg Mn/g protein of acid washed flour | Percent Mn Removal |
|---|---|---|
| 0 | 59 | 77 |
| 1 | 49 | 81 |
| 2 | 40 | 85 |
| 3 | 34 | 87 |

Thus, addition of calcium during acid washing of rice flour is another aspect of the instant process of the invention. In this regard, the step of blending rice flour and water at a pH of 3.4 to 4.6 is carried out by adding calcium salts to the rice flour at a concentration of 0.1 to 3.6% and preferably 0.3 to 1% calculated on the basis of calcium content.

Resuspending the washed rice flour, adjusting the suspension to a pH and temperature within the operable range of an alpha-amylase enzyme and treating with the enzyme to hydrolyze the starch—steps (Ac) and (Ad)

Following acid washing, the resuspended washed rice flour is gelatinized and enzymatically hydrolyzed essentially as described by the aforementioned prior art to effect partial liquification of the rice starch for separation from the treated rice flour. In general, liquification (solubilization) is conventionally carried out by resuspending the washed rice flour in water providing a pumpable slurry with a solid content generally in the range from about 15-30%, preferably 20% by weight. The pH of the slurry is adjusted to within the operable range of the enzyme, generally about 5.5 to 9.0 and preferably to a pH of 6.2 to 7.0, with a base such as potassium hydroxide and relatively heat-stable alpha-amylase enzyme such as Termamyl (Novo Laboratories, Inc., Wilton, CT) or Takalite (Miles, Inc., Elkhart, IN) added with the mixture subjected to elevated temperatures on the order of 75° to 100° C. and preferably about 90° C. with adequate mixing.

As will be appreciated by those skilled in the art, different amylases may be used with appropriate process variations. For instance, with Termamyl or Takalite, about 0.3% enzyme is used based on the weight of unwashed rice flour. Higher enzyme levels allow shorter reaction time, or reverse. Temperatures may vary from below room temperature to over 100° C. and the reaction time accordingly adjusted since the rate of enzyme activity varies with temperature. The length of amylase treatment is determined by the degree of starch hydrolysis required to achieve acceptable HPRF protein level.

Heating and stirring are continued until the enzymatic hydrolysis of the starch has proceeded to 5-50 dextrose equivalent (DE), preferably 20-35 DE and most preferably 24-30 DE syrup. DE is an index relating to ability to function as a reducing sugar. As such, it constitutes a measure of the total reducing power of the carbohydrate source expressed as anhydrous dextrose and calculated as a percent of the total solids. At 5-50 DE, the rice starch has been sufficiently hydrolyzed (i.e. liquified) to provide (on separating the mixture) rice flour (HPRF) with an increased protein level of 16% or above, preferably 16 to 60%, on a dry weight basis. Infant formula at protein level of 14 grams per quart can be made with HPRF protein content as low as 16% protein. At levels below 16% protein, complete infant formula are difficult to make because of the amount of flour required to provide the desired protein level. However, this does not preclude using the instant HPRF low Mn process to produce flour at levels of 10%-16% protein for use in infant food supplements which also require low manganese content.

Adjusting the enzyme treated reaction mixture to pH 3.4 to 4.6 and separating the HPRF from syrup—steps (Ae) and (Af)

When the targeted DE content has been achieved, the amylase is inactivated by adding acid, preferably by adjusting the pH to about 3.4 to 4.6, and most preferably to pH 3.8, with temperature maintained at about 90° C. Selection of the acid is not critical with food grade acids preferably employed. Phosphoric acid is most preferred as it does not contribute off flavor and relatively small amounts are required compared to weaker acids such as acetic or citric. Following enzyme inactivation by pH adjustment, the solubilized (i.e. hydrolyzed) rice starch is separated from the insoluble HPRF by conventional means such as centrifugation, filtration, or decantation. If desired, the wet HPRF can be washed with water to remove additional rice syrup and manganese retained in the wet cake. Further the solubilized rice syrup fraction is useful in its own right and although it must be removed from the rice flour to provide the instant HPRF, it constitutes an economically valuable commodity as a food source. For example, in the infant formula of the instant invention, an appropriate amount of rice carbohydrate can be added to the HPRF to provide required carbohydrate levels.

Aside from enzyme inactivation, adjustment to acid pH is critical with respect to further removal of manganese from HPRF. This additional reduction in manganese is necessary since if the Mn present in the washed rice flour exceeded a level of 35 to 50 mcg/g protein and was retained by the HPRF, the amount of Mn in finished infant formula would exceed desired levels. As previously mentioned, the maximum NAS-FNB Estimated Safe and Adequate Daily Dietary Intake of manganese for infants is 700 mcg/day. Assuming one quart of formula per day as average consumption, infant formulas should then have no more than 700 mcg manganese/qt. The following calculation establishes the maximum allowable ad desired manganese levels in washed rice flour assuming no further removal during the separation of HPRF from syrup.

| CALCULATION 2 | |
|---|---|
| Maximum Allowable Manganese Levels in Washed Rice Flour (700 mcg/qt ÷ grams protein) | |
| Grams Protein | Manganese/g Protein |
| 14 | 50 mcg |
| 20 | 35 mcg |

It is evident that without further removal of manganese, washed rice flour having manganese levels of above 35-50 mcg/g protein cannot be used since the resulting infant formula would have unacceptable manganese levels.

As previously mentioned, the acceptable upper manganese levels of rice flour is 50 mcg/g protein with less preferred. Lower levels cannot be obtained without extensive acid washing of the rice flour prior to enzyme treatment. This is not required in the instant process since by adjusting the mixture to a pH between 3.4-4.6 or preferably at pH 3.6-4.0 and more preferably 3.8 with a food grade acid prior to separation of HPRF from syrup, the manganese content of the HPRF is reduced. This pH adjustment is critical to providing HPRF having a manganese content of less than about 50 mcg per gram protein. The amount of manganese contributed by the HPRF to a quart of infant formula containing 14-20 grams protein is illustrated by the following calculation.

| CALCULATION 3 | | |
|---|---|---|
| Manganese Provided by HPRF Per Quart Formula (grams protein/qt × mcg Mn/g protein) | | |
| Mn Content of | Micrograms Mn per quart at | |
| HPRF (mcg/g protein) | 14 g | 20 g |
| 50 | 700 | 1000 |
| 40 | 560 | 800 |
| 30 | 420 | 600 |
| 20 | 280 | 400 |
| 10 | 140 | 200 |
| 5 | 70 | 100 |

As previously mentioned, maximum manganese levels provided by the instant low manganese HPRF are 700mcg per quart formula. Thus, HPRF having a manganese content of about 50 mcg/g protein or less is required with a preferred level of no more than about 30. Preferred ranges in micrograms manganese per gram protein are 5 to 50 and 10 to 30. As will be appreciated by those skilled in the art, in the event the instant lower manganese HPRF does not provide sufficient manganese for the minimum recommended daily amount, appropriate amounts of manganese can be added to the formula.

The combined effect of adjusting the enzyme treated acid washed rice flour (1:9 rice flour-water) and rice syrup separation (1:4 washed rice flour-water) is shown in Table 3 below.

TABLE 3

Manganese Content of High Protein Rice Flour (mcg Mn/g protein) Using Various pH's for Acid Wash and Syrup Separation

| Acid Wash pH | Rice Syrup Separation pH | | |
|---|---|---|---|
| | 5.5 | 4.5 | 3.5 |
| 4.5 | 56.6 | 18.2 | 16.0 |
| 4.0 | 36.6 | 17.9 | 14.4 |
| 3.5 | 37.3 | 16.1 | 9.3 |

It is evident that the final Mn content of HPRF is dependent on the particular selection of both the pH of the acid wash and rice syrup seperation. For example, acceptable manganese content can be obtained at separation of the rice syrup at 3.5 to 5.5 with acid wash at 3.5 to 4.0 but not at 4.5 acid wash. According to the instant process, at the operable acid wash range pH 3.4 to 4.6, separation of rice syrup is preferably carried out at 3.4 to 4.6 following enzyme treatment.

Typical manganese levels for 1800 pound batches of 8% protein rice flour (originally assaying for 263 micrograms per gram protein) washed with 16,200 pounds of water at pH 3.5 and subsequently gelatinized and enzyme treated with separation of the HPRF and rice syrup at a pH of 3.5 are shown below in Table 4 below along with comparative manganese levels obtained with syrup separation at pH 6.0.

TABLE 4

Manganese Content (mcg/g protein) of Acid Washed Flour and of HPRF

| Batch | Acid Washed Flour | High Protein Rice Flour Separated from Rice Syrup at: | |
|---|---|---|---|
| | | pH 3.5 | pH 6.0 |
| A | 53.6 | 7.3 | |
| B | 61.9 | 9.5 | |
| C | 61.9 | 9.1 | |
| D | 64.3 | 9.8 | |
| E | 64.3 | 9.3 | |
| F | 54.8 | 9.3 | |
| G | 61.9 | 9.3 | |
| H | 61.9 | 10.5 | |
| I | 56.0 | 8.9 | |
| J | 53.6 | 8.0 | |
| K | 69.0 | | 52.3 |
| L | 53.6 | | 53.6 |

The Mn content of HPRF is 11 mcg or less per gram HPRF when syrup separation is carried out at pH 3.5. Batch results vary to some extent according to centrifuge efficiency in separating the syrup. The results illustrate that satisfactory HPRF Mn levels can be obtained from acid washed rice flour when separation of the rice syrup is carried out at a pH of 3.5. As previously mentioned, below pH 3.4, the separated rice syrup contains significant amounts of solubilized rice protein thereby reducing the yield of low manganese HPRF.

Alternate process for preparing high protein rice flour (HPRF) with significantly reduced manganese content In the process for preparing HPRF discussed above (Process A), manganese is removed at two stages. The first stage involves washing rice flour at acid pH with substantial removal of manganese (about 70-80%) with or without addition of calcium salts. Remaining manganese is concentrated in the HPRF obtained by enzymatic hydrolysis of the rice carbohydrate and, unless the rice flour manganese content has been reduced to 5 to 50 mcg/g protein or preferably 10 to 30 mcg/g protein by extensive washing, further separation of manganese is required. This is carried out at a second stage by separating the enzymatically hydrolyzed rice carbohydrate from HPRF under specific acid pH conditions.

In the instant alternate process (herein Process B) the rice flour is first enzymatically hydrolyzed, then separated from rice syrup at neutral pH and the high manganese HPRF finally washed at acid pH to remove manganese. Thus, in accordance with the instant invention, there is provided an alternate process for preparing high protein rice flour (HPRF) with substantially reduced manganese content from rice flour containing manganese which comprises the steps of:

(Ba) treating said rice flour with an alpha-amylase enzyme for a sufficient time to hydrolyze the starch to 5 to 50 DE content;

(Bb) separating high manganese HPRF from rice syrup at neutral pH;

(Bc) resuspending the high manganese HPRF in water at pH 3.4 to 4.6; and (Bd) removing the acid wash water to provide low manganese high protein rice flour.

Steps (Ba) and (Bb) of Process B are conventional, essentially following the teachings of Hansen, et al., Chen, et al., and Chang, et al., supra. In practice, previously described conditions for carrying out the rice carbohydrate enzymatic hydrolysis of Process A are applicable and preferred. At step (Bb) there is relatively little separation of manganese from HPRF with only negligible levels of manganese present in the rice syrup. For example, 25% protein HPRF obtained from 8.5% protein rice flour with a manganese content of 165-175 mcg/g protein has a manganese level of about 168 mcg/g protein whereas the separated rice syrup contains only about 0.1 mcg/g solids.

As previously shown, the manganese content of rice flour varies considerably with levels ranging typically from 150 to 260 mcg/g protein. The HPRF in Step (Bb) will essentially contain the same manganese content as the original flour on a protein basis since there is no significant separation at neutral pH.

Also, as previously mentioned, a quart of formula typically contains from 14 to 20 g protein with desired maximum manganese level of less than 700 microgram per qt. Thus, in the above illustration, the HPRF from Step (Bb) provides from 2352 mcg to 3360 mcg of manganese per quart and cannot be used in infant formula.

Steps (Bc) and (Bd) are carried out under conditions described for the first stage of manganese removal in Process A, i.e. steps (Aa) and (Ab). After the step (Bb) rice syrup separation in Process B, the HPRF is resuspended in water to provide a pumpable slurry with an HPRF ratio (parts by weight) of about 1:3 to 16 preferred and a ratio of 1:9 most preferred and pH adjusted to 3.4 to 4.6 with food-grade acids (e.g., phosphoric, hydrochloric, nitric, sulfuric, citric, acetic, and the like). The separated acid washed HPRF has manganese levels similar to those found in Process A.

While Process B provides HPRF with significantly reduced manganese levels, there are several disadvantages inherent in the alternate process compared to Process A. The acid wash of HPRF produces a rice syrup with high manganese during step (Bd). This leads to greater problems in waste disposal of the spent acid wash containing the rice carbohydrate. In addition the yield of useful rice syrup is reduced.

High protein rice flour (HPRF) dispersibility and mouthfeel improvement (modified low manganese HPRF)

Low manganese high protein rice flour obtained by Process A or B of the instant invention is suitable as a basic ingredient for non-liquid foodstuffs but further processing is required to provide characteristics appropriate for use in infant formula. In particular, protein dispersibility and mouthfeel must be improved. With respect to dispersibility, the grainy mouthfeel of infant formula using HPRF obtained according to the prior art primarily reflects HPRF protein insolubility at the pH of infant formula. Moreover, because of the grainy texture, the low manganese HPRF obtained according to Process A or B cannot be easily given in an infant formula since feeding nipples tend to quickly plug up.

Modification of the low manganese HPRF protein to eliminate graininess and improve mouthfeel is carried out by treatment with a proteolytic enzyme. Complete solubilization of the HPRF protein is not necessary to improve dispersibility and mouthfeel and is to be avoided as extensive protease modification improves solubility but with development of an unpleasant bitter flavor.

There are a number of different proteases which can be used for this modification. These may include neutral bacterial proteases (e.g., Neutrase), alkaline bacterial proteases (e.g., Alcalase), fungal proteases, animal proteases (e.g., trypsin, pancreatin), or plant proteases (e.g., papain, ficin, bromelain). For ease of processing, it is preferable to select a protease which has a pH optimum near neutral pH, relatively easy to inactivate, and commercially available at reasonable cost.

Preferably, the enzyme Neutrase (Novo, Inc., Wilton, CT) is used as it does not produce a bitter off-flavor and is inactivated near pasteurization temperature. Thus, in accordance with the instant invention, there is provided a process for improving protein dispersibility and mouthfeel of low manganese high protein rice flour wherein said flour contains from 16 to 60% protein and 5 to 50 microgram manganese per gram protein which comprises the steps of:

(a) adjusting a slurry of said low manganese HPRF to pH 5.5 to 8 and temperature of 40° to 60° C.;
(b) adding a proteolytic enzyme;
(c) stirring the mixture for a sufficient period to hydrolyze from 1-5% of the peptide bonds; and then
(d) heating the mixture to inactivate the proteolytic enzyme.

Preferred process conditions are:

Step (a)—slurry adjusted to pH 6.0 with base (e.g., potassium hydroxide) with temperature of 50° C;
Step (b)—adding the proteolytic enzyme at 0.5 to 2% and preferably a 1% concentration based on protein content of HPRF;
Step (c)—stir mixture 30 minutes;
Step (d)—heating the mixture to 70° C. to 80° C. for 10 minutes to inactivate the enzyme.

The above proteolytic processed high protein rice flour with reduced manganese can be spray dried by conventional means to provide a modified high protein rice flour containing 50 mcg or less manganese per gram protein with improved dispersability and mouthfeel as a powder base for an infant formula. Alternatively, it can be incorporated into an infant formula base and then spray dried to provide powdered infant formula. Or, it can be incorporated into a shelf stable liquid formula.

As will be appreciated by those skilled in the art, numerous variations of the above process are possible. For example, longer reaction time allows use of lower enzyme concentration, lower temperature requires a longer reaction time, etc. The desired peptide hydrolysis of 1% to 5% (preferably 2% to 3%) is determined by measuring the increase in free amino groups by a conventional primary amino group assay such as the method of Habeeb, Anal. Biochem. 14:328 (1966).

Comparative organoleptic testing of the mouthfeel of infant formula made with and without protease treatment was carried out. On a 5 to 1 scale where a score of 5 would mean a smooth mouthfeel and a score of 1 grainy, sandy, or mealy mouthfeel, product made without protease received a score of 2. With protease treatment, the instant formula received a score of 4.

The proteolytic modified high protein rice flour (HPRF) with reduced manganese (Mn) of the instant invention can be used to prepare a complete infant formula that meets the nutritional requirements for infants as described by the infant Formula Act of 1980. (Public Law 96-359, Sept. 26, 1980). The term "complete infant formula" means a food which purports to be or is represented for special dietary use solely as a food for infants by reason of its simulation of human milk or its suitability as a complete or partial substitute for human milk. The protein levels in complete infant formula vary from 1.8 to 4.5 g per 100 kcal. Since 640 kcal/qt is the average caloric content of human milk and infant formula and the range of protein in infant formula is 11.5 to 28.8 g per quart, then the protein caloric range is 7.2% to 18% of total calories.

In the instant formula, a protein range of 14 to 20 g of protein per quart is preferred with the protein source comprising modified low Mn HPRF containing 16-60% protein and 5 to 50 mcg Mn/g protein. The protein levels found in low manganese HPRF may vary depending on the conditions used for starch hydrolysis and the efficiency of the separation process. For example, the more water retained in the HPRF the lower the protein content. The proteolytic modified low Mn HPRF contains manganese at levels less than 50 mcg per gram protein and the reconstituted product contains no more than 700 mcg Mn/qt (NAS-FNB).

In a typical formulation, the modified HPRF contains 44% protein and 10 mcg Mn/g protein. About 42.3 g of HPRF is needed to provide 18.6 g. of protein per quart. This modified HPRF with low Mn content thus provides 186 mcg Mn/qt which is about 15 to 25 times less Mn than a similar formula using HPRF prepared according to the prior art.

Optionally, the HPRF can be supplemented with the amino acids, lysine and threonine at levels of 2.75 and 6 g HPRF protein, respectively, to increase the PER from 70% casein without supplementation to 110% of casein with supplementation. The amino acid addition is not required but increases the nutritional value of the rice protein in the infant formula.

The carbohydrate portion of this infant formula may be any edible FDA approved carbohydrate that is readily digested by the infant. This carbohydrate may include lactose, sucrose, corn syrup solids, or rice syrup solids. Since the HPRF process produces a large quantity of by-product rice syrup solids that is easily digested by the infant, it is preferably used to adjust the carbohydrate levels to 28 to 63% of total calories required for a complete infant formula.

The lipid portion of the formula is made up of edible FDA approved oils or blends of oil which are generally recognized as appropriate for infant feeding. The total fat concentration of the infant formula is about 30 to 54% of calories and is usually made up of vegetable oils such as corn oil, soybean oil, coconut oil, or safflower oil. The lipid composition provides a fatty acid distribution similar to human milk and contains appropriate levels of linoleic acid, an essential fatty acid.

A powdered infant formula base is prepared by dispersing the modified HPRF in water together with rice syrup, minerals, and an oil blend. The mixture is heated to 75° C. and conventionally homogenized in a two stage piston-type homogenizer at 2500 and 500 psi pressure to develop a stable liquid emulsion. The concentrated liquid (at about 40% solids) is spray dried and then dry blended with the vitamin-amino acid premix and trace mineral premix to provide finished formula powder. Generally, about 124-128 grams is used to make 1 qt of reconstituted product but the amount may be varied in accord with good nutritional practice.

The vitamin and mineral levels are similar to commercially marketed infant formulas and conform to the levels recommended by the Infant Formula Act of 1980.

Infant formula based on HPRF is unique because it contains no milk protein, no soy protein, no lactose, no sucrose, and no corn syrup solids. The instant formula provides levels of protein, carbohydrate, fat, vitamins, minerals, and trace elements based on recognized infant nutritional requirements and standards. Because of its unique composition, it can be used by infants with allergies to cow milk protein or soy protein, by infants with lactose or sucrose intolerance as well as by healthy, normal infants to provide desired growth and development in all children.

The following examples further illustrate the manner in which various aspects of the invention may be carried out.

EXAMPLE 1

Manganese Removal From Rice Flour by Washing-pH and Dilution Effects

Eight percent protein rice flour (180 g, Riviana Foods, Inc., Houston, TX) containing 166 mcg manganese per gram protein was suspended in 420 grams distilled water at ambient temperature (about 22°-25° C.). The flour to water ratio employed has an effect on the amount of water soluble manganese retained by the washed flour with the amount of water soluble manganese remaining in the washed flour generally decreased by employing more water relative to flour. The pH of the suspension is 6.1. Five identical suspensions were prepared and adjusted to a pH of 3.5, 4.0, 4.5, 5.0 and 5.5 with 1N hydrochloric acid.

The flour suspensions were stirred for a period of 60 minutes and the flour collected by centrifugation using 2000 gravity (g)-minutes (min) (average). The supernatant was removed and a fraction of the flour pellet dried and analyzed for manganese using atomic absorption spectrometry. The remainder of the flour was then resuspended in distilled water to yield a flour to water ratio (parts by weight) of 3:7 and adjusted to test pH with 1N hydrochloric acid as required. The suspensions were then stirred for a 15 minute period and centrifuged as above. Samples of the collected flour were analyzed for manganese and the above rewash procedure repeated once again. There are no significant differences with respect to manganese removal between shorter or longer stirring times as long as thorough mixing is achieved. Findings are reported in Table 5 below.

TABLE 5

| Wash pH | Effect of pH on Washed Flour Manganese Content (microgram per gram protein) | | |
|---|---|---|---|
| | Number of Washes | | |
| | 1 | 2 | 3 |
| "As is" (6.1) | 169 | 159 | 121 |
| 5.5 | 123 | 55 | 21 |
| 5.0 | 90 | 40 | 25 |
| 4.5 | 54 | 18 | 13 |
| 4.0 | 64 | 20 | 11 |
| 3.5 | 56 | — | — |

This study illustrates that manganese removal is dependent on the ratio of flour to water as reflected by the number of washes and is most effectively removed from rice flour at wash pH values of 3.5 to 5.5 with the amount of water soluble manganese retained by the washed flour decreasing as a higher ratio of water to flour is used. For example, at pH 4.0, 180 grams of flour was washed in a total of 1260 grams of water which represents an overall ratio (parts by weight) of 1 part flour to 7 parts water thereby providing "washed" rice flour with a manganese level of 11 microgram per gram protein. Preferably, the flour is washed at a pH of 3.4-4.6 to reduce the manganese content to the desired level of less than 50 microgram per gram protein.

EXAMPLE 2

Manganese Removal From Rice Flour By Washing—Temperature Effect

Aliquots of 8% protein rice flour (40 g, Riviana Foods, Inc., Houston, Tex.) containing 225 mcg manganese per gram protein were suspended in 360 grams distilled water at 10°, 23°, 30°, 35° or 45° C. The pH was adjusted to 3.5 with 1N hydrochloric acid and the flour suspensions maintained at the designated temperatures for a 30 minute period with stirring. Suspensions were then centrifuged for 6000 g-min (average), the supernatant removed and the washed flour dried and analyzed for manganese using atomic absorption spectrometry. Findings are reported in Table 6 below.

TABLE 6

| Effect of Temperature on Washed Flour Manganese Content | |
|---|---|
| Wash Temperatures (°C.) | Microgram per gram protein |
| 10 | 58 |
| 23 | 56 |
| 30 | 60 |
| 35 | 59 |
| 45 | 55 |

This study indicates that the temperature of the extraction is not critical with respect to removal of manganese. Thus, temperatures below the point of gelatinization of the rice flour can be employed in the instant process with ambient temperature preferred from a convenience and operability standpoint.

EXAMPLE 3

Manganese Removal From Rice Flour by Washing—Acidulant Effect

Three aliquots of 20 g of 8% protein rice flour (Riviana Foods, Inc., Houston, TX) containing 200 mcg manganese per gram protein were suspended in 180 grams of distilled water at ambient temperature. The suspensions were adjusted to a pH of 3.5 with 1N hydrochloric acid, 1N citric acid, 1N phosphoric acid. After stirring for 30 minutes, the washed flour was collected by centrifugation for 6000 g-min (average). The supernatant was removed and the washed flour dried and analyzed for manganese using atomic absorption spectrometry. Findings are reported in Table 7 below.

TABLE 7

| Effect of Acidulant on Flour Manganese Content | |
|---|---|
| Acidulant | Microgram per gram protein |
| Hydrochloric Acid | 51 |
| Citric Acid | 53 |
| Phosphoric Acid | 48 |

This study demonstrates that both organic and inorganic acid can be employed as acidulants in the instant process without significantly affecting efficiency of the manganese extraction.

EXAMPLE 4

Manganese Removal From Rice Flour by Washing—Particle Size Effect

Aliquots (20 g) of rice of varied particle size were washed with 180 grams water (rice:water ratio of 1:9). Samples consisted of (a) 100 mesh rice flour (Riviana Foods, Inc., Houston, Tex.), (b) rice grits (Riviana Foods., Inc., Houston Tex., 30 mesh) and (c) whole kernel rice (Coors Food Products, Weiner, Ark.). The same quantity of 1N hydrochloric acid was added to each sample to provide an adjusted pH of 3.5±0.5. The suspensions were stirred at room temperature for 2.5 hours with samples drawn at 15, 30, 60, 90, 120 and 150 minutes. The collected samples were centrifuged for 6000 g-min (average), dried and analyzed for manganese using atomic absorption spectrometry. Findings are reported in Table 8 below with efficiency of the manganese removal calculated on a percent removed.

TABLE 8

Effect of Rice Particle Size on Washed Flour Manganese Removal

| | Manganese Content and Percent Efficiency at Wash Time | | | |
|---|---|---|---|---|
| | 15 min | | 30–150 min[a] | |
| Sample | mg/g protein | (efficiency) | mcg/g protein | (efficiency) |
| Flour[b] | 44 | (78%) | 35 | (82%) |
| Grits[c] | 23 | (78%) | 15 | (85%) |
| Whole Kernel[d] | 35 | (78%) | 29 | (82%) |

[a]Determined by averaging Mn values obtained at 30 minute intervals
[b]100 Mesh - 195 mcg Mn/g protein
[c]30 Mesh - 104 mcg Mn/g protein
[d]Polished rice (bran removed) - 159 mcg Mn/g protein The results illustrate that particle size of rice raw material is not a significant controlling factor with respect to efficiency of reducing manganese by acid washing.

EXAMPLE 5

Manganese Removal From Rice Flour by Washing—Calcium Salt Effect

Aliquots (20 g) of 8% protein rice flour (Riviana Foods, Inc., Houston, TX) containing 213 microgram manganese per gram protein were suspended in 180 grams distilled water. A calcium salt selected from the group of calcium chloride, calcium phosphate monobasic, calcium phosphate dibasic and calcium phosphate tribasic was added to an aliquot to give a calcium to flour ratios ranging from 0.181 to 0.722 g calcium per 100 g flour and the rice flour-calcium salt suspensions stirred at ambient temperature for a period of five minutes. The pH of the suspensions were then adjusted to 3.5 with 1N phosphoric acid with stirring continued at ambient temperature for a period of 30 minutes. The flour was collected by centrifugation for 6000 g-min (average), the supernatent removed and the washed rice flour dried and analyzed using atomic absorption spectrometry. Findings are reported in Table 9 below.

TABLE 9

Effect of Caliium Salts on Manganese Content of Washed Flour

| Calcium Salt | g Calcium/ 100 g Flour | Flour Manganese Content (Microgram per gram protein) |
|---|---|---|
| None | — | 58 |
| Calcium Chloride | 0.722 | 33 |
| Monobasic Calcium Phosphate | 0.181 | 39 |
| Monobasic Calcium Phosphate | 0.361 | 38 |
| Monobasic Calcium Phosphate | 0.722 | 28 |
| Monobasic Calcium Phosphate | 1.083 | 40 |
| Dibasic Calcium Phosphate | 0.361 | 31 |
| Dibasic Calcium Phosphate | 0.722 | 31 |
| Tribasic Calcium Phosphate | 0.361 | 35 |
| Tribasic Calcium Phosphate | 0.722 | 33 |

This study demonstrates that calcium chloride and calcium phosphate significantly enhances manganese removal from washed flour at acidic pH and a calcium salt to flour ratio of as little as 0.18 grams calcium per 100 grams flour.

EXAMPLE 6

Low Manganese High Protein Rice Flour

Whole grain milled rice flour (150 parts by weight) having a protein content of 8 percent and a manganese content of about 200 microgram per gram protein and water (1350 parts by weight) were blended in a tank with high shear agitation with adjustment of pH to 3.8 with phosphoric acid. The pH adjusted slurry was then pumped to a Sharples P3400 Superdecanter (Sharples-Stokes Div., Pennwalt Corp., Warminster, Pa.) centrifuge at 25 gallons per minute (GPM) flow rate. The protein containing residue from the centrifuge was resuspended in water, pumped to a second tank and sufficient water added to provide a slurry of 20% solids with adjustment to pH 6.2 with potassium hydroxide. After adjusting the pH, 0.58 parts by weight of amylase enzyme Takalite L-340 (Miles, Inc., Elkhart, Ind.) was added to the slurry. The slurry was then heated to 90° C. by means of a scraped-surface heat exchanger and held for 20 minutes, pH adjusted to 3.8 with phosphoric acid and stirred at high temperature for an additional 10 minutes to inactivate the amylase enzyme. The slurry was centrifuged at 10–15 GPM flow rate to provide a high protein rice flour with substantially reduced manganese content of 9 microgram per gram protein, a protein content of about 44 percent and a carbohydrate content of 53 percent.

EXAMPLE 7

Alternate Process for Preparing High Protein Rice Flour (HPRF) With Significantly Reduced Manganese Content Rice flour (150 parts by weight, containing 8.0% protein and 250 microgram manganese per gram protein) is suspended in 600 parts by weight water at ambient temperature (about 22°-25° C.). After adjusting the pH to 6.2 with potassium hydroxide, 0.58 parts by weight of amylase enzyme Takalite L-340 (Miles, Inc., Elkhart, Ind.) is added to the slurry. The slurry is then heated to 90° C. by means of a scraped-surface heat exchanger and held for 20-30 minutes to hydrolyze the rice starch to 24 to 30 DE content and centrifuged. The high protein rice flour contains from 40 to 45% protein and about 227 microgram of manganese per gram protein and is resuspended in 1350 parts water with adjustment of pH to 3.5 to 4.5. Following mixing, the mixture is separated to provide low manganese high protein rice flour containing about 60% protein on a dry weight basis and about 10 micrograms of manganese per gram protein.

EXAMPLE 8

Rice Syrup

The rice syrup supernatent from the centrifugal separation of low manganese high protein rice flour of Example 6 had a DE of 24–30 and was concentrated from 22% solids to 60%, then spray dried to yield 100 parts by weight of rice syrup solids having a manganese content of 2–3 microgram per gram solids, a carbohydrate content of 98.3% and less than 1% protein.

EXAMPLE 9

Low Manganese High Protein Rice Flour With Improved Dispersibility and Mouthfeel The low manganese high protein rice flour of Example 6 was resuspended in water at 15–20% solids, pH of the rice protein slurry adjusted to pH 6.0 with potassium hydroxide and heated to 50° C. A proteolytic enzyme, Neutrase 0.5L (Novo, Inc.), was added at a rate of 0.14 parts by weight (about 1% on protein basis) and stirred for 30 minutes. The rice protein slurry was heat treated at 75° C. for 10 minutes to inactivate the proteolytic enzyme. The modified high protein rice flour with reduced manganese can be spray dried or incorporated into an infant formula base and then spray dried if desired. Approximately 25 lbs. of low manganese (9 mcg/g protein) high protein rice flour at 44% protein with improved dispersibility and mouthfeel was produced from 150 lbs. of the rice flour starting material used in Example 6.

EXAMPLE 10

Preparation of Nutritional Powder Rice Formula

The Example 9 modified low manganese high protein rice flour product (332.35 pounds) and 328.65 pounds of rice syrup solids (DE 30) are dispersed in 1434 pounds water at about 55° C. A major mineral mix (total 29.2 pounds) is added to the dispersion followed by 266.1 pounds of an oil blend consisting of 55% corn oil and 45% coconut oil. The mixture is heated to 70°-75° C. for about 8 minutes and then homogenized in a two-stage homogenizer at pressures of 2500 and 500 psi. The homogenized material is spray dried to provide 980 g of solids containing about 2.5% water which is then dry-blended with 8.7 pounds of a vitamin-amino acid premix, 0.45 pounds trace mineral premix, and 10.85 pounds of rice syrup solids containing about 98-99% carbohydrate and 0.2 to 0.4% protein.

The major mineral premix contains the following substances

| Ingredient | Parts by weight |
| --- | --- |
| Calcium carbonate | 13.3 |
| Potassium phosphate dibasic | 5.8 |
| Sodium citrate | 5.3 |
| magnesium phosphate dibasic | 3.6 |
| Sodium chloride | 0.9 |
| Potassium citrate | 0.4 |

The vitamin-amino acid premix contains the following substances per 100 parts by weight of dry material:

| Ingredient | Parts by weight |
| --- | --- |
| Lysine HCl | 60.0549 |
| L-Threonine | 10.4960 |
| Sodium ascorbate | 8.0871 |
| Rice dextrins | 4.9781 |
| DL-Alpha tocopheryl acetate | 4.3829 |
| Taurine | 4.1548 |
| Inositol | 3.1535 |
| Vitamin $D_1$, dry | 1.3682 |
| Vitamin A, 250A | 1.0234 |
| Niacinamide | 0.8399 |
| Biotin, 1% trituration | 0.5728 |
| Calcium pantothenate | 0.3654 |
| Vitamin $B_{12}$ | 0.2097 |
| Vitamin $D_3$, 400D | 0.1190 |
| Riboflavin | 0.0634 |
| Thiamine hydrochloride | 0.0578 |
| Pyridoxine hydrochloride | 0.0510 |
| Folic acid | 0.0128 |
| Potassium iodide | 0.0093 |

The trace mineral premix contains the following substances per 100 parts by weight of dry material:

| Ingredient | Parts by weight |
| --- | --- |
| Iron ($Fe_2SO_4.7H_2O$) | 16.86 |
| Zinc sulfate | 9.94 |
| Cupric sulfate | 0.76 |

EXAMPLE 11

Reconstituted Rice Powder Formula

The rice formula powder product of Example 10 is reconstituted by dispersing 127.2 g to 1 quart volume in water to provide a ready-to-use rice based infant formula having the following typical composition:

| Composition | Reconstituted Rice Formula Quantity in 1 Qt. Formula* | Manganese Content | Manganese mcg/Quart |
| --- | --- | --- | --- |
| Rice protein concentrate (44% protein, 53% carb.) | 42.3 g | 9 mcg Mn/g protein | 167.5 |
| Rice syrup solids (0.3% protein, 98.3% carb.) | 43.2 g | 2.3 mcg Mn/g solids | 99.4 |
| Oils | 33.8 g | 0 | 0 |

-continued

| Composition | Reconstituted Rice Formula | | |
|---|---|---|---|
| | Quantity in 1 Qt. Formula* | Manganese Content | Manganese mcg/Quart |
| Minerals | 3.7 g | 10 mcg Mn/g | 37 |
| Vitamins | 1.1 g | 0 | 0 |
| Total Manganese | | | 273.9 mcg |

*on a solids basis

What is claimed is:

1. Low manganese high protein rice flour comprising high protein rice flour containing more than 16 percent protein and manganese content of 50 micrograms or less per gram of protein.

2. Low manganese high protein rice flour of claim 1 comprising high protein rice flour containing from 16 to 60 percent protein and from 5 to 50 micrograms of manganese per gram of protein.

3. Low manganese high protein rice flour of claim 1 comprising high protein rice flour containing from 16 to 60 percent protein and 10 to 30 micrograms of manganese per gram protein.

4. A process for preparing high protein rice flour with substantially reduced manganese content from rice flour containing manganese which comprises the steps of:
   (Aa) blending rice flour and water at a pH of 3.4 to 4.6;
   (Ab) separating the insoluble washed rice flour of step (Aa);
   (Ac) resuspending the washed rice flour of step (Ab) and adjusting the suspension to a pH and temperature within the operable range of an alpha-amylase enzyme;
   (Ad) treating the suspension of step (Ac) with an alpha-amylase enzyme for a sufficient time to hydrolyze the starch to 5 to 5% DE content;
   (Ae) adjusting the treated mixture of step (Ad) to pH of 3.4 to 4.6; and then
   (Af) separating rice syrup from low manganese high protein rice flour.

5. The process of claim 4 wherein separating the rice syrup provides low manganese rice flour with a protein content of more than 16 percent.

6. The process of claim 4 wherein separating the rice syrup provides low manganese rice flour with a manganese content of from 5 to 50 microgram per gram of protein.

7. The process of claim 4 wherein separating the rice syrup provides low manganese rice flour with a protein content of from 16 to 60 percent.

8. The process of claim 4 wherein the rice flour contains from 150 to 260 micrograms manganese per gram protein before blending.

9. The process of claim 4 wherein rice flour and water are blended at a flour-water ratio of 1:3 to 1:20 parts by weight.

10. The process of claim 4 wherein rice flour and water are blended at a flour-water ratio of 1:6 to 1:12 parts by weight.

11. The process of claim 4 wherein rice flour and water are blended at a flour-water ratio of 1:9 parts by weight.

12. The process of claim 4 wherein rice flour and water are blended at pH of 3.8 to 4.2.

13. The process of claim 4 wherein rice flour and water are blended with from 0.1 to 3.6% calcium at a pH of 3.4 to 4.6.

14. The process of claim 4 wherein rice flour and water are blended with from 0.3 to 1? calcium at a pH of 3.4 to 4.6.

15. The process of claim 4 wherein the resuspended washed rice flour is adjusted to a pH of 5.5 to 9.0.

16. The process of claim 4 wherein the resuspended washed rice flour is adjusted to a pH of 6.0 to 7.0.

17. The process of claim 4 wherein the rice starch is hydrolyzed to 20 to 35 DE content.

18. The process of claim 4 wherein the rice starch is hydrolyzed to 24 to 30 DE content.

19. The process of claim 4 wherein the alpha-amylase enzyme treated suspension is adjusted to pH 3.6 to 4.0 by adding acid prior to separating rice syrup.

20. The process of claim 4 wherein the alpha-amylase enzyme treated suspension is adjusted to pH 3.8 by adding acid prior to separating rice syrup.

21. The process of claim 20 wherein phosphoric acid is used for pH adjustment.

22. A process for preparing low manganese high protein rice flour from rice flour containing no more than 50 mcg manganese per gram which comprises the steps of:
   (Ba) treating said rice flour with an alpha-amylase enzyme for a sufficient time to hydrolyze the starch to 5 to 50 DE content;
   (Bb) separating high manganese HPRF from rice syrup at neutral pH;
   (Bc) resuspending the high manganese HPRF in water at pH 3.4 to 4.6; and
   (Bd) removing the acid wash water to provide low manganese high protein rice flour.

23. The process of claim 22 wherein the protein content of the high protein rice flour is from 16 to 60 percent and the manganese content is from 5 to 50 microgram per gram of protein.

24. A process for improving dispersibility and mouth-feel of low manganese high protein rice flour containing from 16 to 60% protein and from 5 to 50 micrograms manganese per gram of protein which comprises the steps of:
   (a) adjusting a slurry of said low manganese HPRF to pH 5.5 to 8 and temperature of 40° to 60° C.;
   (b) adding a proteolytic enzyme;
   (c) stirring the mixture for a sufficient period to hydrolyze from 1 to 5% of the peptide; and then
   (d) heating the mixture to inactivate the proteolytic enzyme.

25. The process of claim 24 wherein said low manganese HPRF contains from 16 to 60% protein and 10 to 30 micrograms manganese per gram protein.

26. A nutritionally complete powdered infant formula comprising modified low manganese high protein rice flour containing from 16 to 60% protein and from 5 to 50 micrograms manganese per gram of protein as the protein source in combination with the required amounts of fat, carbohydrates, minerals and vitamins wherein the reconstituted formula contains 14 to 20 grams of protein and 70 to 700 micrograms of manganese per quart.

* * * * *